US011893659B2

(12) United States Patent
Rijken et al.

(10) Patent No.: US 11,893,659 B2
(45) Date of Patent: Feb. 6, 2024

(54) DOMAIN ADAPTION (71) Applicant: Kheiron Medical Technologies Ltd., London (GB)

(72) Inventors: Tobias Rijken, London (GB); Michael O'Neill, London (GB); Andreas Heindl, London (GB); Joseph Yearsley, London (GB); Dimitrios Korkinof, London (GB); Galvin Khara, London (GB)

(73) Assignee: Kheiron Medical Technologies Ltd., London (GB)

( * ) Notice: Subject to any disclaimer, the term of this patent is extended or adjusted under 35 U.S.C. 154(b) by 499 days.

(21) Appl. No.: 17/309,275

(22) PCT Filed: Nov. 27, 2019

(86) PCT No.: PCT/GB2019/053342
§ 371 (c)(1),
(2) Date: May 13, 2021

(87) PCT Pub. No.: WO2020/109781
PCT Pub. Date: Jun. 4, 2020

(65) Prior Publication Data
US 2022/0020184 A1 Jan. 20, 2022

(30) Foreign Application Priority Data

Nov. 29, 2018 (GB) ..................................... 1819434

(51) Int. Cl.
*G06T 11/00* (2006.01)
*G06T 7/00* (2017.01)
(52) U.S. Cl.
CPC .......... *G06T 11/003* (2013.01); *G06T 7/0012* (2013.01); *G06T 2207/30068* (2013.01)

(58) Field of Classification Search
CPC ........................... G06T 11/003; G06T 7/0012
See application file for complete search history.

(56) References Cited

U.S. PATENT DOCUMENTS

2002/0194159 A1* 12/2002 Kamath .............. G06F 16/2465
2018/0330205 A1* 11/2018 Wu ........................ G06N 3/02
(Continued)

OTHER PUBLICATIONS

Becker et al., "Injecting and removing malignant features in mammography with CycleGAN: Investigation of an automated adversarial attack using neural networks," arxiv.org, Cornell University Library, 201Olin Library Cornell University Ithaca, NY 14853, Nov. 19, 2018 (Nov. 19, 2018), pp. 1-7.
(Continued)

*Primary Examiner* — Kevin Ky
(74) *Attorney, Agent, or Firm* — Luedeka Neely, P.C.

(57) ABSTRACT

The present invention relates to a method and system that allows input mammography images to be converted between domains. More particularly, the present invention relates to converting mammography images from the image style common to one manufacturer of imaging equipment to the image style common to another manufacturer of imaging equipment. Aspects and/or embodiments seek to provide a method of converting input images from the format output by one imaging device into the format normally output by another imaging device. The imaging devices may differ in their manufacturer, model or configuration such that they produce different styles of image, even if presented with the same raw input data, due to the image processing used in the imaging device(s).

11 Claims, 7 Drawing Sheets

(56) References Cited

U.S. PATENT DOCUMENTS

| | | | |
|---|---|---|---|
| 2019/0295302 A1* | 9/2019 | Fu | G06V 10/82 |
| 2019/0354801 A1* | 11/2019 | Sohn | G06V 40/172 |
| 2020/0020098 A1 | 1/2020 | Odry et al. | |
| 2020/0303072 A1* | 9/2020 | Drokin | G16H 10/60 |
| 2021/0012198 A1* | 1/2021 | Zhang | G06N 3/08 |
| 2022/0020184 A1* | 1/2022 | Rijken | A61B 6/502 |

OTHER PUBLICATIONS

Choi et al, "StarGAN: Unified Generative Adversarial Networks for Multi-Domain Image-to-Image Translation," Sep. 21, 2018 (Sep. 21, 2018), Retrieved from the Internet: URL:https://arxiv.org/pdf/1711.09020.pdf [retrieved on Nov. 12, 2019].

Korkinof et al "High-Resolution Mammogram Synthesis using Progressive Generative Adversarial Networks," arxiv.org, Cornell University Library, 201 Olin Library Cornell University Ithaca, NY 14853, Jul. 9, 2018 (Jul. 9, 2018).

Zhu et al., "Unpaired Image-to-Image Translation using Cycle-Consistent Adversarial Networks ", arxiv.org, Cornell University Library, 201 Olin Library Cornell University Ithaca, NY 14853, Mar. 30, 2017 (Mar. 30, 2017).

\* cited by examiner

DOMAIN ADAPTION

FIELD

The present invention relates to a method and system that allows input mammography images to be converted between domains, i.e. performing domain adaption in mammography. More particularly, the present invention relates to converting mammography images from the image style common to one manufacturer of imaging equipment to the image style common to another manufacturer of imaging equipment using Generative Adversarial Networks.

BACKGROUND

Mammography is a medical imaging modality widely used for breast cancer detection. Mammography makes use of "soft" X-rays to produce detailed images of the internal structure of the human breast. These images are called mammograms and this method is considered to be the gold standard in early detection of breast abnormalities which provide a valid diagnosis of a cancer in a curable phase.

Unfortunately, the procedure of analysing mammograms is often challenging. The density and tissue type of the breasts are highly varied and in turn present a high variety of visual features due to patient genetics. These background visual patterns can obscure the often-tiny signs of malignancies which may then be easily overlooked by the human eye. Thus, the analyses of mammograms even by highly skilled human operators, typically specialist doctors, often lead to false-positive or false-negative diagnostic results which may cause missed treatment (in the case of false-negatives) as well as unwanted psychological and sub-optimal downstream diagnostic and treatment consequences (in the case of false-positives).

Most developed countries maintain a population-wide screening program, a comprehensive system for calling in women of a certain age group, free of symptoms to have regular breast screening. These screening programs require highly standardized protocols to be followed by experienced specialist trained doctors who can reliably analyse a large number of mammograms routinely. Most professional guidelines strongly suggest reading of each mammogram by two equally expert radiologists (industrially known as double-reading). Nowadays, with the number of available highly skilled radiologists scarce and decreasing, the double-reading requirement is often impractical or impossible.

As such, computer aided diagnosis is becoming more popular as techniques improve. Typically, the current state of the art techniques for computer aided diagnosis use machine learning to provide the high level of reliability required to be deployed in a clinical setting. To achieve this level of reliability, the machine learning algorithms need to be trained on data sets that allow reliable operation. However, there are many manufacturers of imaging devices and so it is necessary to train models/algorithms on training data from each imaging device with which the trained algorithm is to be used, but this isn't always possible and new imaging devices are being developed and launched commercially thus it is an ongoing problem that models/algorithms need to be trained on training data using images for each existing and new imaging device in order to be reliable.

Training models/algorithms in one domain (i.e. on a set of image data sourced from one manufacturer's imaging device) and then using these trained models/algorithms in another domain (i.e. on image data from another manufacturer's imaging device) can result in the models/algorithms not performing well in the other domain.

SUMMARY OF THE INVENTION

Aspects and/or embodiments seek to provide a method of converting input images from the format output by one imaging device into the format normally output by another imaging device. The imaging devices may differ in their manufacturer, model or configuration such that they produce different styles of image, even if presented with the same raw input data, due to the image processing used in the imaging device(s).

According to a first aspect, there is provided a computer-aided method of training a neural network to transfer mammography images between domains, the neural network operable to perform the steps of: receiving a plurality of mammogram images in a first domain; receiving a plurality of mammogram images in a second domain; determining a first network to transfer one or more of the plurality of mammogram images in a first domain to a second domain to output transferred second domain images; determining a second network to transfer one or more of the plurality of mammogram images in a second domain to a first domain to output transferred first domain images; determining a discriminator network to output labels for each input image, the labels comprising being in the first domain, being in the second domain or being a generated image; wherein the training of the neural network is performed by optimising a sum of losses.

By training a network constructed in this way, it is possible to train a network to transfer input mammography images between a first and second domain.

Optionally, each of the first and/or second networks to transfer one or more of the plurality of images between domains comprises a paired encoder and decoder By using a paired encoder and decoder, the encoder can learn an abstract representation of the features of the input image and the decoder can learn how to translate the abstract representation of fractures into a domain specific image.

Optionally, optimising a sum of losses comprises optimising a sum of losses between at least a plurality of: each of the plurality of mammogram images in a first domain; each of the plurality of mammogram images in a second domain, each of the labels; each of the output transferred second domain images; and each of the output transferred second domain images.

Optionally, the neural network is operable to receive at least one further plurality of mammogram images in one or more further domains and at least one further network to transfer one or more of the plurality of mammogram images in one of the domains to another of the domains to output transferred another of the domains' images.

More than a first and second domain can be trained using this structure of network and approach, so third, fourth etc. domains can be trained.

Optionally, each of the losses making up the sum of the losses is weighted relative to each other of the losses making up the sum of the losses.

By applying weights to each of the losses that make up the sum of losses, the training process and/or network(s) can be fine-tuned.

Optionally, the training of the neural network is first done using low resolution image data then iteratively in one or more steps the resolution of the image data is increased as the neural network is trained.

By using progressively growing techniques, the network can be trained more efficiently or effectively.

Optionally, the losses making up the sum of the losses includes any combination of: a breast mask loss; a consistency loss; a reconstruction loss; a vendor loss; and a GAN loss.

Optionally, any of the first and/or second networks to transfer one of more of the plurality of images between domains comprises a generative network.

Optionally, the first domain is a first vendor image style and the second domain is a second vendor image style.

According to a second aspect, there is provided a trained network to transfer one or more of the plurality of mammogram images in one domain to another domain, trained according to the method of any preceding claim.

By outputting a trained network, optionally a trained encoder-decoder pair, the trained network can be used to transfer images between domains, for example from one manufacturer image format to another.

BRIEF DESCRIPTION OF DRAWINGS

Embodiments will now be described, by way of example only and with reference to the accompanying drawings having like-reference numerals, in which.

SPECIFIC DESCRIPTION

Figure 7:
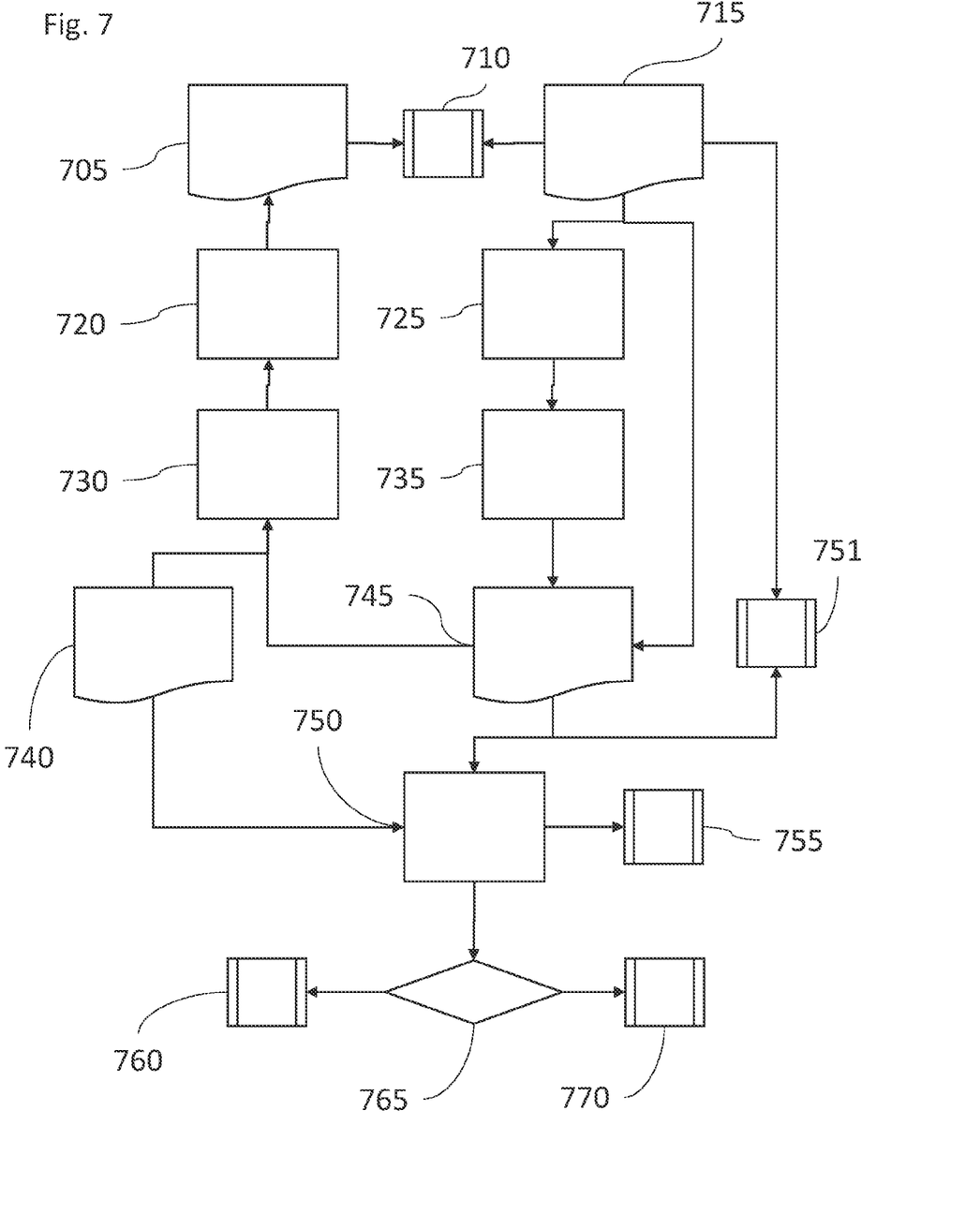
FIG. 7 illustrates an implementation of the method according to aspects/embodiment(s) described in more detail below.

FIG. 7 depicts an example embodiment of the present invention, which will be described below in more detail.

Figure 1:
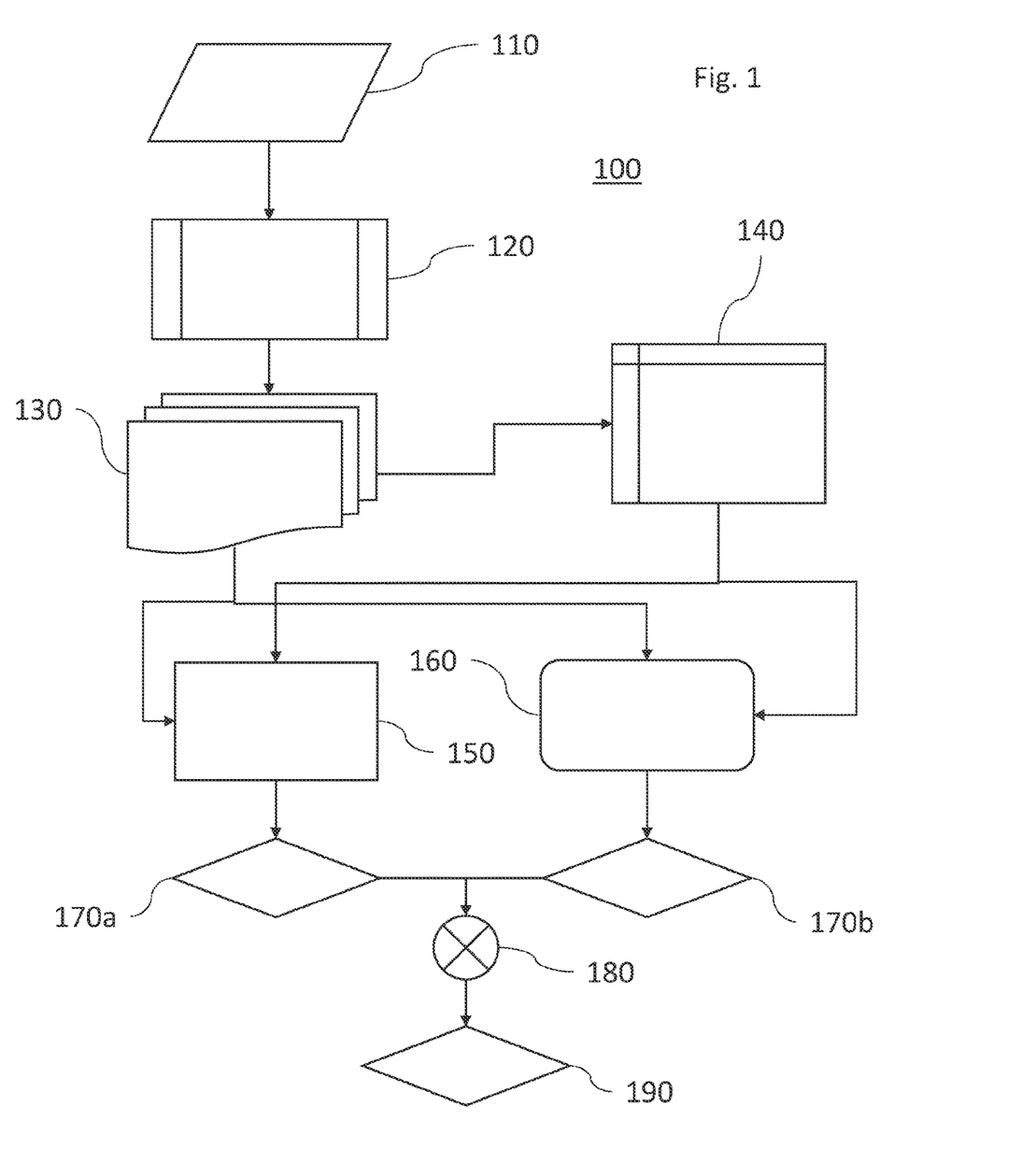
FIG. 1 illustrates an example flowchart showing a typical method used to perform mammography.

Referring first to FIG. 1, there is shown a typical process for analysing and/or diagnosing a patient, or patients, using the mammography process. Image data 110 is gathered using an imaging device (not shown). The imaging device is a "soft" x-ray device. The imaging devices can be from multiple manufacturers, and each manufacturer has a proprietary method/software/process/algorithm 120 for converting the raw input image data 110 gathered by the x-ray sensor into image data 130 that can be understood by a human operator. Due to the proprietary nature of this process 120 for producing the image data 130, the output image data 130 varies subtly between imaging devices. Also, as over time manufacturers may change their proprietary method/software/process/algorithm 120, it is possible that an older imaging device may differ slightly in the output image data 130 from a new version of that imaging device from the same manufacturer, or alternatively compared to a different model of imaging device from the same manufacturer regardless of whether the original sensor image data 110 being exactly the same between models and/or manufacturers.

It may be worth noting that the detectors/sensors that generate the raw input image data 110 are to a great extent commoditised. The main difference between imaging devices from different manufacturers is the proprietary post-processing software/method/algorithm 120 that converts the raw input image data 110 into the output image data 130. In some examples it is possible for the human eye to determine the different "styles" of image output from imaging devices from different manufacturers.

The output image data 130 is usually stored in a PACS (Picture Archiving & Communications System) 140, which is a data server for patient data and in particular medical imaging data which is typically stored in the DICOM format.

The output image data 130 is either then sent for review 150, 160 directly, or is at a later point in time extracted from the PACS 140 for review 150,160. Typically, each review 150, 160 is carried out by an independent trained specialist medical professional, a radiologist, who has been trained to identify potentially malignant features/portions in the patient images 130. This provides two independent review of each case, i.e. image data 130 associated with each patient. The PACS 140 may sometimes also provide historical image data 130 related to each case, i.e. from previous scans for each patient, either automatically or on request.

In some cases, the second review 160 is carried out by an automated system. The automated system typically is a machine learned process using neural networks trained on sample data from imaging devices.

Each of the reviews 150, 160 output a respective decision 170a, 170b (and optionally some metadata relevant to the decision, e.g. if malignancy is diagnosed an area of one or more images supporting this diagnosis may be annotated or highlighted). The combination of these decisions 180 is handled in different ways depending on the risk tolerance of the respective medical professionals, but in the majority of cases if either decision 170a, 170b indicates that there is a diagnosis of malignancy then the final decision 190 is that malignancy is present in the patient and further medical interventions are needed.

Figure 6:
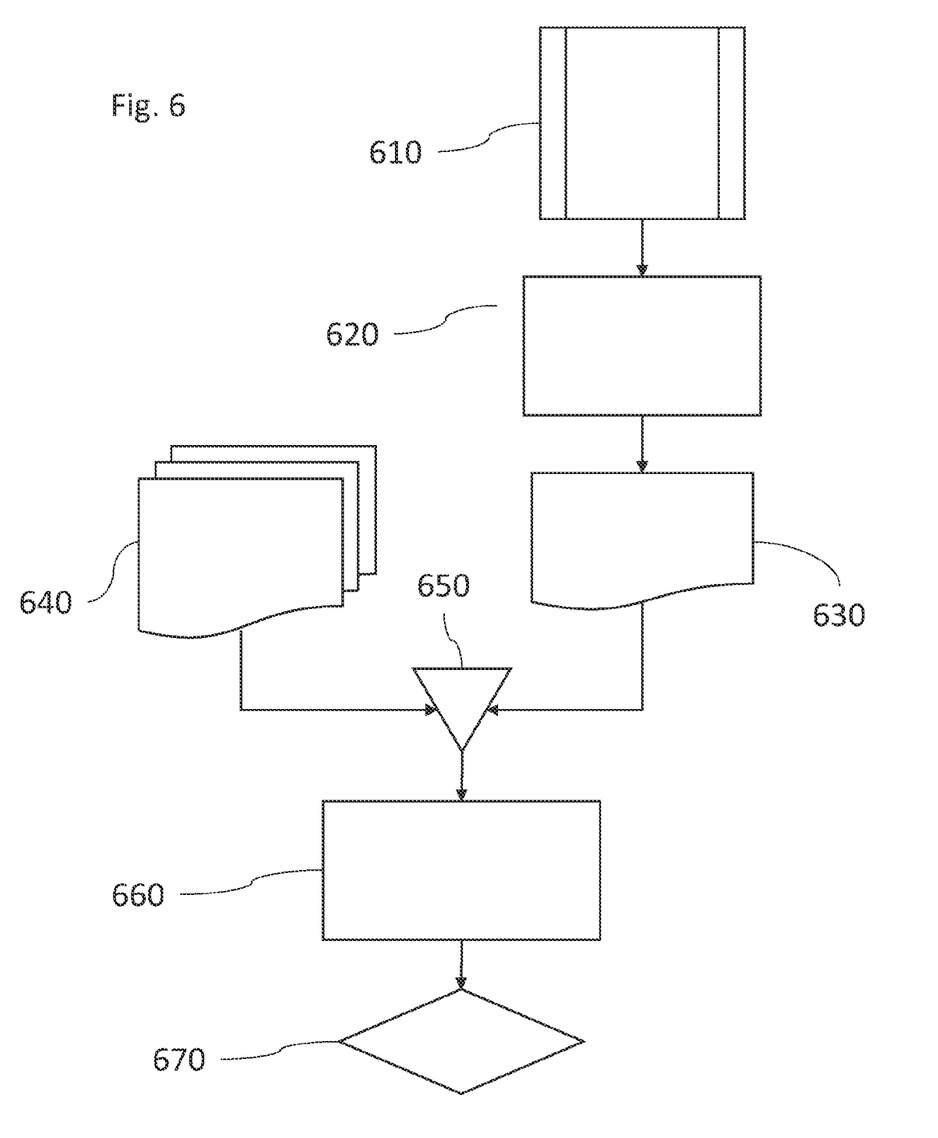
FIG. 6 illustrates an implementation of a generative adversarial network used in aspects or embodiments.

Referring now to FIG. 6, Generative Adversarial Networks (or GANs) will now be briefly described.

In this example, the GAN will deal with images. Random noise 610 is generated as an input into the system shown in FIG. 6. The random noise 610 is input into a generator network 620, which outputs fake images 630. The fake images 630 are fed into a discriminator network 660 in parallel 650 with some real images 640. The discriminator network 660 outputs whether it labels 670 each input image as real or fake.

The generator network 620, or generator, tries to predict features for a given input. It functions to generate new data, in this example fake image data. The discriminator network 660, or discriminator, tries to predict a label (e.g. real or fake) for each input. The goal of training the system of FIG. 6 is for the generator 620 to produce fake images that are recognised as authentic/real by the discriminator 660.

To train the system, the discriminator 660 is in a feedback loop that can assess its labels against the ground truth of whether each input image 650 was real or fake and the label 670 output by the discriminator 660 for each input image 650. Further, the generator 620 is in a feedback loop with the discriminator 660 so that it receives data on whether the discriminator 660 output a real or fake label 670 for the input image 650. The system as a whole is trained together, sometimes by allowing each of the generator 620 and discriminator 660 to learn separately, and optionally by pre-training the discriminator 660 before training the generator 620, and optionally by freezing the values/weights on each of the discriminator 660 or generator 620 while training the other.

A more detailed introduction to GANs, which is hereby incorporated by reference, can be found at https://towardsdatascience.com/generative-adversarial-networks-gans-a-beginners-guide-5b38eceece24. Further implementations of GANs are described in the following papers, which are also hereby incorporated by reference:

the "StarGAN" approach: https://arxiv.org/pdf/1711.09020.pdf;
the "CycleGAN" approach: https://arxiv.org/pdf/1703.10593.pdf; and
the "PGGAN" approach: https://arxiv.org/pdf/1710.10196.pdf.

Referring to FIG. 7, a specific embodiment will now be described.

One or more first domain images 715, e.g. images from an imaging device from a first manufacturer, is taken as one input to the network of FIG. 7. Each first domain image 715 is fed into a first paired encoder 725 and decoder 735, which output a fake second domain image 745 where the domain of the first domain image has attempted to be transferred to a second domain. A loss is calculated between each first domain image 715 and each respective fake second domain image 745 called the breast mask loss 751.

The fake second domain image 745 is then fed back into a second paired encoder 730 and decoder 720 to output a fake first domain image 705. The weights of the first and second paired encoders 725, 730 and decoders 735, 720 are the same. A loss termed the reconstruction loss 710 is calculated between each first domain image 715 and each respective fake first domain image 705 reconstructed from the fake second domain image 745.

In alternative embodiments further domains may be included, requiring further encoder-decoder pairs, and these encoder-decoder pairs maintain the same weights as the first and second paired encoders 725, 730 and decoders 735, 720.

Each fake second domain image 745 and one or more second domain images 740 are fed into a discriminator 750. A loss termed the consistency loss 755 is calculated between each fake second domain image 745 and each second domain image 740. The discriminator 750 labels 765 each input image as either in the first or second domains or a fake image. The loss between the labels for the first or second domains is calculated as the vendor loss 770 and the loss between the labels for the first or second domains and the label that one or more images are fake is calculated as the GAN loss 760.

The total loss is a weighted sum of the breast mask loss 751, the reconstruction loss 710, the filter loss 755, the vendor loss 770 and the GAN loss 760.

The network in FIG. 7 is trained to converge on a solution that optimises the total loss. More specifically, the training is done in a progressively growing fashion, that is to say that the training starts with images of a very low resolution until the network has been trained. Then successive extra layers are added to the network, each incrementally increasing the resolution of the images involved, until the network has been trained to handle the full desired resolution to be processed.

The network described above in effect learns the features that are vendor specific so that it can manipulate these features and transfer across domains. The result is an image-to-image or domain-to-domain translation model where one can input, for example, a first vendor image into the relevant trained encoder-decoder pair and the network outputs an image of the same mammogram, but it now looks like a second vendor image (or any other manufacturer on which the network has been trained). Thus, the purpose of the network is to keep the key content the same but change the "vendor features".

If one has access to the raw detector data, transferring between image domains would be simple. If one has access to a referenced set of a first vendor image, a second vendor image and a raw detector image of the same breast, one could learn the mapping function from vendor A to raw image to vendor B. However, it is not possible to have access to the raw detector images nor the proprietary algorithms/processing techniques used by each vendor, nor is there any known sufficiently large dataset containing images from multiple vendors for the same patient. Instead the approach described in the specific embodiment can substantially automatically learn the vendor features from a large dataset of images.

Referring now to FIGS. 2 to 5, examples of the use of the specific embodiment to adapt the domains of the imaging data 130 of patients is shown.

Figure 2:
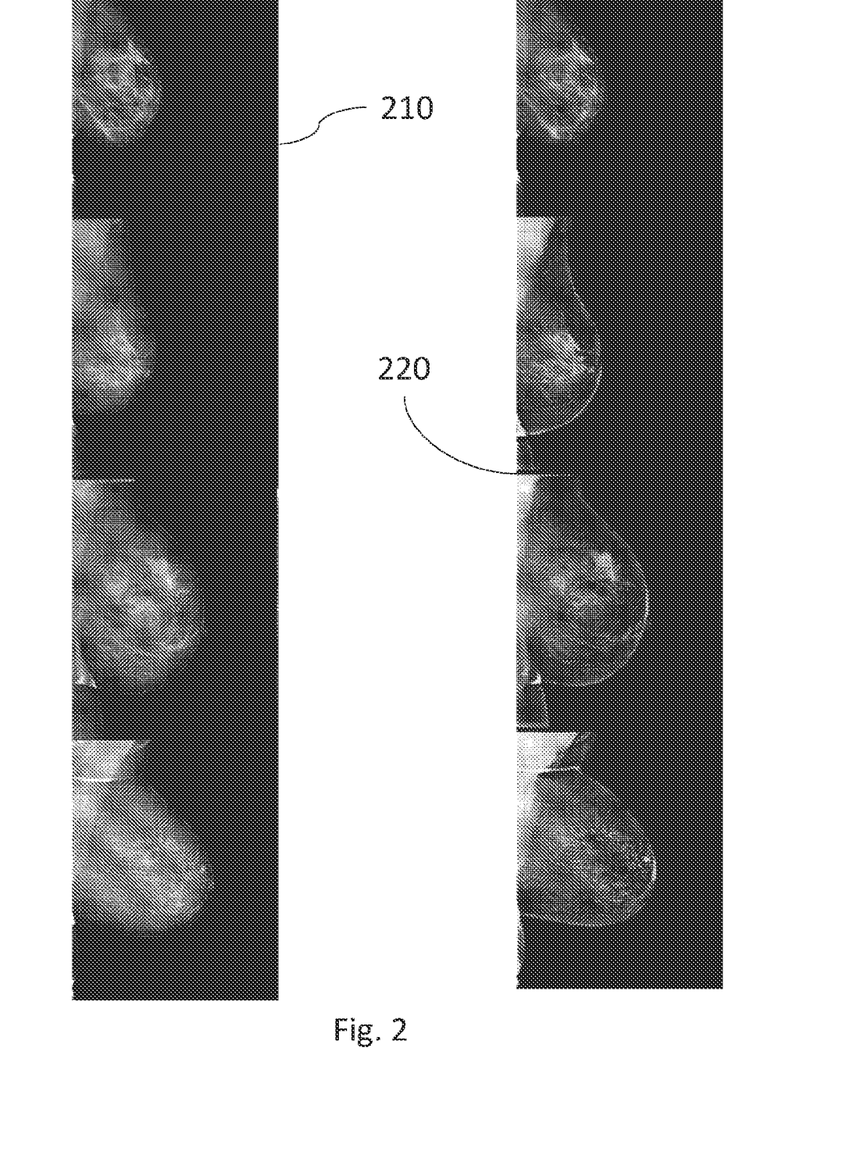
FIGS. 2 to 5 illustrate a set of input images in the style of the output of devices from one imaging device manufacturer being converted using the method of the aspects/embodiments into the style of the output of devices from another imaging device manufacturer.

Specifically, in FIG. 2, the four mammography images 210 shown on the left-hand side are real images taken with a second vendor imaging device and the images 220 shown on the right-hand side are the domain transferred images having used the method of the specific embodiment to transfer the domain from a second vendor image style to a generated first vendor style of image.

Figure 3:
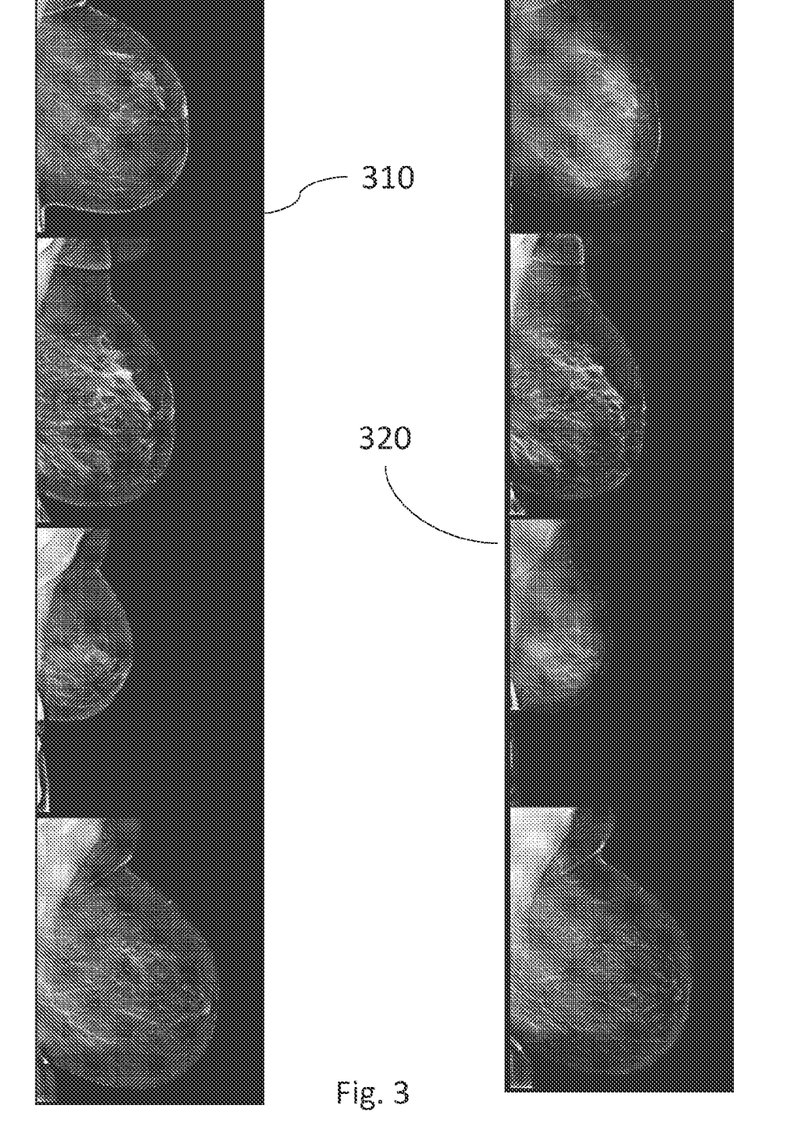

Then, in FIG. 3, the four mammography images 310 shown on the left-hand side are real images taken with a first vendor imaging device and the images 320 shown on the right-hand side are the domain transferred images having used the method of the specific embodiment to transfer the domain from a first vendor image style to a generated second vendor style of image.

Figure 4:
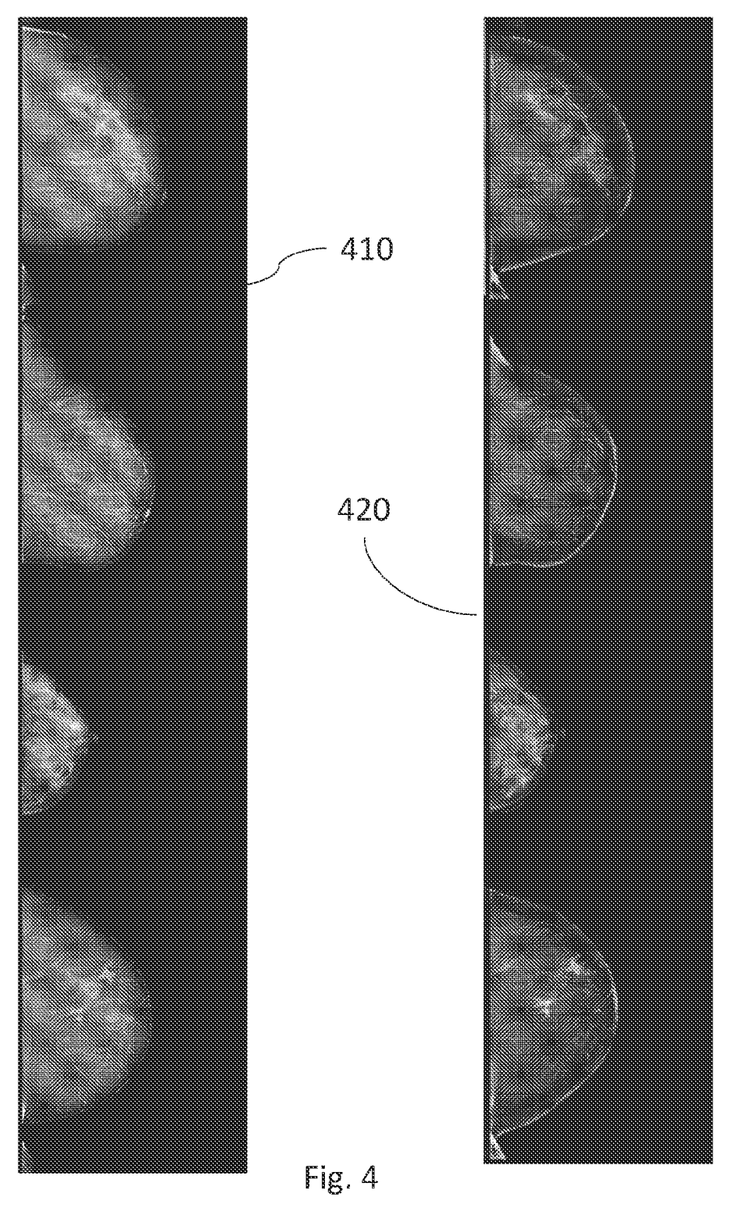

Next, in FIG. 4, the four mammography images 410 shown on the left-hand side are real images taken with a second vendor imaging device and the images 420 shown on the right-hand side are the domain transferred images having used the method of the specific embodiment to transfer the domain from a second vendor image style to a generated first vendor style of image.

Figure 5:
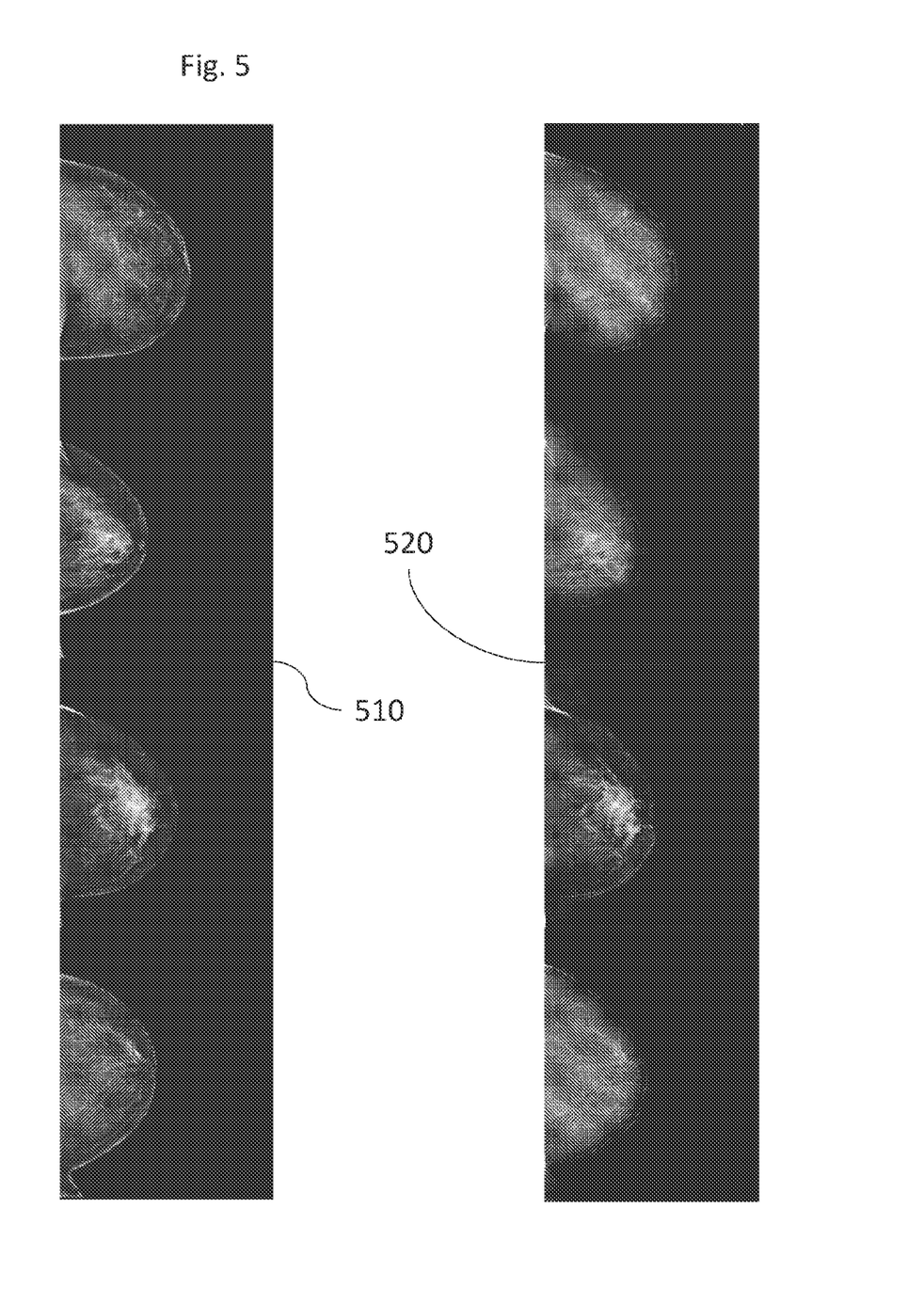

Finally, in FIG. 5, the four mammography images 510 shown on the left-hand side are real images taken with a first vendor imaging device and the images 520 shown on the right-hand side are the domain transferred images having used the method of the specific embodiment to transfer the domain from a first vendor image style to a generated second vendor style of image.

As it is not possible to ascertain how each manufacturer processes 120 the raw input data 110 into an output image 130, the method of the specific embodiment allows for domain transfer without knowledge of any manufacturer processing 120. This therefore allows training of machine learned algorithms/models on image data 130 from only one manufacturer's imaging data to be used with imaging data from other domains/manufacturer's output images 130 as the input images 130 can undergo a domain transformation step prior to analysis by the machine learned algorithm/model.

Machine learning is the field of study where a computer or computers learn to perform classes of tasks using the feedback generated from the experience or data gathered that the machine learning process acquires during computer performance of those tasks.

Typically, machine learning can be broadly classed as supervised and unsupervised approaches, although there are particular approaches such as reinforcement learning and semi-supervised learning which have special rules, techniques and/or approaches. Supervised machine learning is concerned with a computer learning one or more rules or functions to map between example inputs and desired outputs as predetermined by an operator or programmer, usually where a data set containing the inputs is labelled.

Unsupervised learning is concerned with determining a structure for input data, for example when performing pattern recognition, and typically uses unlabelled data sets. Reinforcement learning is concerned with enabling a computer or computers to interact with a dynamic environment, for example when playing a game or driving a vehicle.

Various hybrids of these categories are possible, such as "semi-supervised" machine learning where a training data set has only been partially labelled. For unsupervised machine learning, there is a range of possible applications such as, for example, the application of computer vision techniques to image processing or video enhancement. Unsupervised machine learning is typically applied to solve problems where an unknown data structure might be present in the data. As the data is unlabelled, the machine learning process is required to operate to identify implicit relationships between the data for example by deriving a clustering metric based on internally derived information. For example, an unsupervised learning technique can be used to reduce the dimensionality of a data set and attempt to identify and model relationships between clusters in the data set, and can for example generate measures of cluster membership or identify hubs or nodes in or between clusters (for example using a technique referred to as weighted correlation network analysis, which can be applied to high-dimensional data sets, or using k-means clustering to cluster data by a measure of the Euclidean distance between each datum).

Semi-supervised learning is typically applied to solve problems where there is a partially labelled data set, for example where only a subset of the data is labelled. Semi-supervised machine learning makes use of externally provided labels and objective functions as well as any implicit data relationships. When initially configuring a machine learning system, particularly when using a supervised machine learning approach, the machine learning algorithm can be provided with some training data or a set of training examples, in which each example is typically a pair of an input signal/vector and a desired output value, label (or classification) or signal. The machine learning algorithm analyses the training data and produces a generalised function that can be used with unseen data sets to produce desired output values or signals for the unseen input vectors/signals. The user needs to decide what type of data is to be used as the training data, and to prepare a representative real-world set of data. The user must however take care to ensure that the training data contains enough information to accurately predict desired output values without providing too many features (which can result in too many dimensions being considered by the machine learning process during training, and could also mean that the machine learning process does not converge to good solutions for all or specific examples). The user must also determine the desired structure of the learned or generalised function, for example whether to use support vector machines or decision trees.

The use of unsupervised or semi-supervised machine learning approaches are sometimes used when labelled data is not readily available, or where the system generates new labelled data from unknown data given some initial seed labels.

Machine learning may be performed through the use of one or more of: a non-linear hierarchical algorithm; neural network; convolutional neural network; recurrent neural network; long short-term memory network; multi-dimensional convolutional network; a memory network; fully convolutional network or a gated recurrent network allows a flexible approach when generating the predicted block of visual data. The use of an algorithm with a memory unit such as a long short-term memory network (LSTM), a memory network or a gated recurrent network can keep the state of the predicted blocks from motion compensation processes performed on the same original input frame. The use of these networks can improve computational efficiency and also improve temporal consistency in the motion compensation process across a number of frames, as the algorithm maintains some sort of state or memory of the changes in motion. This can additionally result in a reduction of error rates.

Developing a machine learning system typically consists of two stages: (1) training and (2) production. During the training the parameters of the machine learning model are iteratively changed to optimise a particular learning objective, known as the objective function or the loss. An example in neural network training would be the backpropagation algorithm, which is used in the described embodiment to train the model. Once the model is trained, it can be used in production, where the model takes in an input and produces an output using the trained parameters.

Any system feature as described herein may also be provided as a method feature, and vice versa. As used herein, means plus function features may be expressed alternatively in terms of their corresponding structure.

Any feature in one aspect may be applied to other aspects, in any appropriate combination. In particular, method aspects may be applied to system aspects, and vice versa. Furthermore, any, some and/or all features in one aspect can be applied to any, some and/or all features in any other aspect, in any appropriate combination.

It should also be appreciated that particular combinations of the various features described and defined in any aspects can be implemented and/or supplied and/or used independently.

The invention claimed is:

1. A computer-aided method of training a neural network to transfer mammography images between domains, the neural network operable to perform the steps of:

receiving a plurality of mammogram images in a first domain wherein the first domain is a first vendor image style;

receiving a plurality of mammogram images in a second domain wherein the second domain is a second vendor image style;

determining a first network to transfer one or more of the plurality of mammogram images in a first domain to a second domain to output transferred second domain images;

determining a second network to transfer one or more of the plurality of mammogram images in a second domain to a first domain to output transferred first domain images; and determining a discriminator network to output labels for each input image, the labels comprising being in the first domain, being in the second domain, being the transferred first images or being the transferred second images;

wherein the training of the neural network is performed by optimising a sum of losses.

2. The method of claim 1 wherein each of the first and/or second networks to transfer one or more of the plurality of images between domains comprises a paired encoder and decoder.

3. The method of claim 1 wherein said optimising a sum of losses comprises optimising a sum of losses between at least a plurality of: each of the plurality of mammogram images in a first domain; each of the plurality of mammogram images in a second domain, each of the labels; each of the output transferred second domain images; and each of the output transferred second domain images.

4. The method of claim 1 wherein the neural network is operable to receive at least one further plurality of mammogram images in one or more further domains, wherein the one or more further domains comprise one or more vendor image styles, and at least one further network to transfer one or more of the plurality of mammogram images in one of the first or second domains domains to the one or more further domains to output transferred one or more further domains' images.

5. The method of claim 1 wherein the each of the losses making up the sum of the losses is weighted relative to each other of the losses making up the sum of the losses.

6. The method of claim 1 where the training of the neural network is first done using low resolution image data then iteratively in one or more steps the resolution of the image data is increased as the neural network is trained.

7. The method of claim 1 wherein the losses making up the sum of the losses includes any combination of:
   a loss calculated between the one or more of the plurality of mammogram images in a first domain and each of the transferred second images;
   a loss calculated between the one or more of the plurality of mammogram images in a first domain and each of the transferred first images;
   a loss calculated between the labels for the first or second domains; and
   a loss calculated between the labels for the first or second domains and the labels for transferred first images or transferred second images.

8. The method of claim 1 wherein any of the first and/or second networks to transfer one of more of the plurality of images between domains comprises a generative network.

9. A trained network to transfer one or more of the plurality of mammogram images in one domain to another domain, trained according to the method of claim 1.

10. The method of claim 1 further comprising learning features associated to each domain.

11. The method of claim 10, wherein the features associated are operable to be manipulated and transferred across domains.

* * * * *